United States Patent
Park

(10) Patent No.: US 11,707,194 B2
(45) Date of Patent: Jul. 25, 2023

(54) HANDHELD DEVICE FOR MEASURING MACULAR PIGMENT

(71) Applicant: ZeaVision LLC, Chesterfield, MO (US)

(72) Inventor: Joshua J. Park, Riverside, CA (US)

(73) Assignee: ZeaVision LLC, Chesterfield, MO (US)

( * ) Notice: Subject to any disclaimer, the term of this patent is extended or adjusted under 35 U.S.C. 154(b) by 203 days.

(21) Appl. No.: 17/304,274

(22) Filed: Jun. 17, 2021

(65) Prior Publication Data
US 2021/0393124 A1 Dec. 23, 2021

Related U.S. Application Data

(60) Provisional application No. 62/705,262, filed on Jun. 18, 2020.

(51) Int. Cl.
*A61B 3/12* (2006.01)
*A61B 3/00* (2006.01)

(52) U.S. Cl.
CPC .............. *A61B 3/12* (2013.01); *A61B 3/0008* (2013.01); *A61B 3/0033* (2013.01); *A61B 3/0041* (2013.01)

(58) Field of Classification Search
CPC ....... A61B 3/12; A61B 3/0008; A61B 3/0033; A61B 3/0041; A61B 3/14; A61B 5/161
USPC ......................................................... 351/221
See application file for complete search history.

(56) References Cited

U.S. PATENT DOCUMENTS

| 4,511,228 A | 4/1985 | Von Gierke |
| 4,861,154 A | 8/1989 | Sherwin |
| 4,889,422 A | 12/1989 | Pavlidis |
| 4,940,323 A | 7/1990 | Downing |
| 5,250,965 A | 10/1993 | Abe |
| 5,331,969 A | 7/1994 | Silberstein |

(Continued)

FOREIGN PATENT DOCUMENTS

| EP | 0 215 566 A2 | 3/1987 |
| GB | 1 012 838 A | 12/1965 |

(Continued)

OTHER PUBLICATIONS

Beatty, S. et al., "Macular Pigment Optical Density Measurement: A Novel Compact Instrument," Ophthal. Physical Opt., 20(2):105-111, 2000.

(Continued)

*Primary Examiner* — Mohammed A Hasan
(74) *Attorney, Agent, or Firm* — Nixon Peabody LLP

(57) ABSTRACT

An instrument includes a housing with a lower hand-held portion having a user-input button and a display for displaying an MPOD score for the user. The instrument further includes a viewing tube coupled to the hand-held portion. The viewing tube terminates in an eye cup. The viewing tube is transverse to the lower hand-held portion and transmits light from a light source in a direction toward the macula. The light source is an LED and provides two colored lights alternating at an initial frequency that is not perceptible by the user. The frequency decreases from the initial frequency until the user activates the user-input button in response to a frequency at which the user perceives a flicker of the two colored lights. The frequency at the perceived flicker relates to the MPOD score of the user. The MPOD score correlates to the amount of macular pigment.

20 Claims, 4 Drawing Sheets

(56) References Cited

U.S. PATENT DOCUMENTS

| | | | |
|---|---|---|---|
| 5,381,195 | A | 1/1995 | Rootzen |
| 6,017,122 | A | 1/2000 | Bone |
| 6,315,412 | B1 | 11/2001 | Snodderly |
| RE38,009 | E | 2/2003 | Garnett |
| 6,572,229 | B2 | 6/2003 | Wei |
| 6,578,965 | B2 | 6/2003 | Grant |
| 6,623,117 | B2 | 9/2003 | Shibutani |
| 6,688,744 | B2 | 2/2004 | Wei |
| 6,729,728 | B2 | 5/2004 | Wei |
| 6,834,958 | B2 | 12/2004 | Cornsweet |
| 6,969,856 | B1 | 11/2005 | Hillenbrand |
| 7,156,518 | B2 | 1/2007 | Cornsweet |
| 7,331,669 | B2 | 2/2008 | Elsner |
| 7,390,090 | B2 | 6/2008 | Murray |
| 7,441,896 | B2 | 10/2008 | Bone |
| 7,467,870 | B2 | 12/2008 | Van de Kraats |
| 8,408,702 | B2 | 4/2013 | Gierhart |
| 8,485,664 | B2 | 7/2013 | Rowe |
| 8,876,293 | B2 | 11/2014 | Gierhart |
| 10,506,925 | B2 | 2/2019 | Huter |
| 2001/0031958 | A1 | 10/2001 | Frey |
| 2002/0097379 | A1 | 7/2002 | Goldfain |
| 2003/0004418 | A1 | 1/2003 | Marmorstein |
| 2003/0130579 | A1 | 7/2003 | McClane |
| 2004/0081628 | A1 | 4/2004 | Gierhart |
| 2004/0193068 | A1 | 9/2004 | Burton |
| 2004/0207811 | A1 | 10/2004 | Elsner |
| 2005/0010115 | A1 | 1/2005 | Bone |
| 2005/0110949 | A1 | 5/2005 | Goldfain |
| 2005/0147648 | A1 | 7/2005 | Gierhart |
| 2005/0171212 | A1 | 8/2005 | Gierhart |
| 2005/0182327 | A1 | 8/2005 | Petty |
| 2005/0254008 | A1* | 11/2005 | Ferguson ............ A61B 3/1025 351/205 |
| 2006/0039954 | A1 | 2/2006 | Gierhart |
| 2006/0089411 | A1 | 4/2006 | Gierhart |
| 2006/0227290 | A1 | 10/2006 | Murray |
| 2006/0270739 | A1 | 11/2006 | Johnson |
| 2007/0082066 | A1 | 4/2007 | Gierhart |
| 2007/0252950 | A1* | 11/2007 | Kraats .................... A61B 3/156 351/221 |
| 2010/0097573 | A1 | 4/2010 | Verdooner |
| 2010/0241450 | A1 | 9/2010 | Gierhart |
| 2012/0092619 | A1* | 4/2012 | Rowe .................. A61B 3/0016 351/221 |
| 2012/0257164 | A1 | 10/2012 | Zee |
| 2014/0118698 | A1* | 5/2014 | Gierhart ............... A61B 3/0008 351/222 |

FOREIGN PATENT DOCUMENTS

| | | |
|---|---|---|
| WO | WO 2007/087314 A2 | 8/2007 |
| WO | WO 2007/127134 A2 | 11/2007 |
| WO | WO 2012/051449 A1 | 4/2012 |

OTHER PUBLICATIONS

Berendschot, T. J. et al., "Influence of Lutein Supplementation on Macular Pigment, Assessed with Two Objective Techniques," University Medical Centre Utrecht, Department of Ophthalmology, The Netherlands, Invest. Ophthal. Vis. Sci., 41(11):3322-3326, Oct. 2000.

Berendschot, T. J. M. & van Norren. D., "Objective Determination of the Macular Pigment Optical Density Using Fundus Reflectance Spectroscopy," Department of Ophthalmology, University Medical Centre Utrecht, The Netherlands, 2004.

Berger, J. W. et al., "Age-Related Macular Degeneration," ISBN: 08247-0682-X, 576 pages, Jul. 2002.

Bernstein, P. S. et al., "Resonance Raman Measurement of Macular Carotenoids in the Living Human Eye," Department of Ophthalmology and Visual Sciences, Moran Eye Center, University of Utah School of Medicine, Salt Lake City, USA, 2004.

Bone, R. A. & Landrum, L. T., "Heterochromatic Flicker Photometry," Department of Physics, Florida International University, Miami, USA, Biochem. Biophys., 430(2):137-142, Oct. 15, 2004.

Bour, L. J. et al., "Fundus Photography for Measurement of Macular Pigment Density Distribution in Children," Investigative Ophthalmology & Visual Science, 43(5), May 2002.

Celentano, J. C. et al., "In Vivo Assessment of Retinal Carotenoids: Macular Pigment Detection Techniques and Their Impact on Monitoring Pigment Status," Department of Animal and Nutritional Sciences, University of New Hampshire, Durham, USA, & Department of Psychology and Behavior Sciences, University of Georgia, Athens, USA, American Society for Nutritional Sciences, 2000.

Choi, S. S. et al., "Effect of wavelength on in vivo images of the human cone mosaic," Journal of the Optical Society of America, 22(12), Dec. 2005.

D'Amato, R. & Snyder, J., "Macular Degeneration—The Latest Scientific Discoveries and Treatments for Preserving Your Sight."

Delori, F. C. & Pflibsen, K. P., "Spectral reflectance of the human ocular fundus," Appl. Opt. 28, pp. 1061-1077, 1989.

Delori, F. C. et al., "Macular Pigment Density Measured by Autofluorescence Spectrometry: Comparison with Reflectometry and Heterochromatic Flicker Photometry," Schepens Eye Research Institute, Boston, USA, and Harvard Medical School, Boston, USA, J. Opt. Soc. Am. A., 18(6):1212-1230, Jun. 2001.

Delori, F. C., "Autofluorescence Method to Measure Macular Pigment Optical Densities Fluorometry and Autofluorescence Imaging," Schepens Eye Research Institute and Harvard Medical School, Boston, USA, 2004.

Gabel, V. P. et al., "Visible and near infrared light absorption in pigment epithelium and choroid," Excerpta Medica, International Congress Series, ElseVier, Amsterdam, No. 450, pp. 658-662, 1978.

Hammond, B. R., Jr. et al., "Assessment of the Validity of In Vivo Methods of Measuring Human Macular Pigment Optical Density," Vision Science Laboratory, University of Georgia, Athens, USA, Optom. Vis. Sci., 82(5):287-404, May 2005.

Handelman, G. J. et al., "Biological control of primate macular pigment, Biochemical and densitometric studies," Invest. Ophthalmol. Vis. Sci. 32, pp. 257-267, 1991.

Mellerio, J. et al., "A Portable Instrument for Measuring Macular Pigment with Central Fixation," Current Eye Research, 25(1):37-47, 2002.

Mellerio, J., "Macular Pigment," Property of the University of Westminster, Vision Research Group, Feb. 2004.

Moreland, J. D., "Macular Pigment Assessment by Motion Photometry," MacKay Institute, Keele University, Staffordshire, Biochem. Biophys., 430(2):143-148, Oct. 15, 2004.

Osborne, N. O. et al., "Topical Flunarizine Reduces IOP and Protects the Retina against Ishcemia-Excitotoxicity," Investigative Ophthalmology & Visual Science, 43(5):1456, May 2002.

Pokorny, J. et al., "Aging of the human lens," Appl. Opt. 26, pp. 1437-1440, 1987.

Robson, A. G. et al., "Comparison of Fundus Autofluorescence and Minimum-Motion Measurements of Macular Pigment Distribution Profiles Derived From Identical Retinal Areas," Perception vol. 43, 2005.

Snodderly, D. M. et al., "Macular Pigment Measurement by Heterochromatic Flicker Photometry in Order Subjects: The Carotenoids and Age-Related Eye Disease Study," for the AREDS Macular Pigment Study Group, Investigative Ophthalmology & Visual Science, 45(2), Feb. 2004.

Van Assendelft, O. W., "Spectroscopy of hemoglobin derivatives," C.C. Thomas, Springfield, IL, USA, pp. 54-57, 1979.

Van de Kraats, J. et al., "The pathways of light measured in fundus reflectometry," Vision Res. 36, pp. 2229-2247, 1996.

Van de Kraats, J. et al., "Lutein and Zeaxanthin Measured Separately in the Living Human Retina with Fundus Reflectometry," Investigative Ophthalmology & Visual Science, 49(12), Dec. 2008.

Van Norren, D. & Tiemeijer, L. F., "Spectral reflectance of the human eye," Vision Res 26, pp. 313-320, 1986.

Van Norren, D. et al., "Fast and Objective Measurement of Macular Pigment with Natural Pupil," Apr. 30, 2005.

(56) References Cited

OTHER PUBLICATIONS

Wooten, B. R. et al., "A Practical Method for Measuring Macular Pigment Optical Density," Investigation Ophthalmology and Visual Science, 40:2481-2489, 1999.

Zarbin, M. A., "Current Concepts in the Pathogenesis of Age-Related Macular Degeneration," Arch. Ophthalmol. 122, Apr. 2004.

ZeaVision, LLC, Product Brochure: QuantifEye® Macular Pigment Optical Density Measurement (MPOD), Mar. 2010.

International Search Report and Written Opinion in International Application No. PCT/US2021/037863, dated Sep. 20, 2021 (10 pages).

International Search Report and Written Opinion in International Application No. PCT/US2021/037863 dated Oct. 5, 2021 (12 pages).

\* cited by examiner

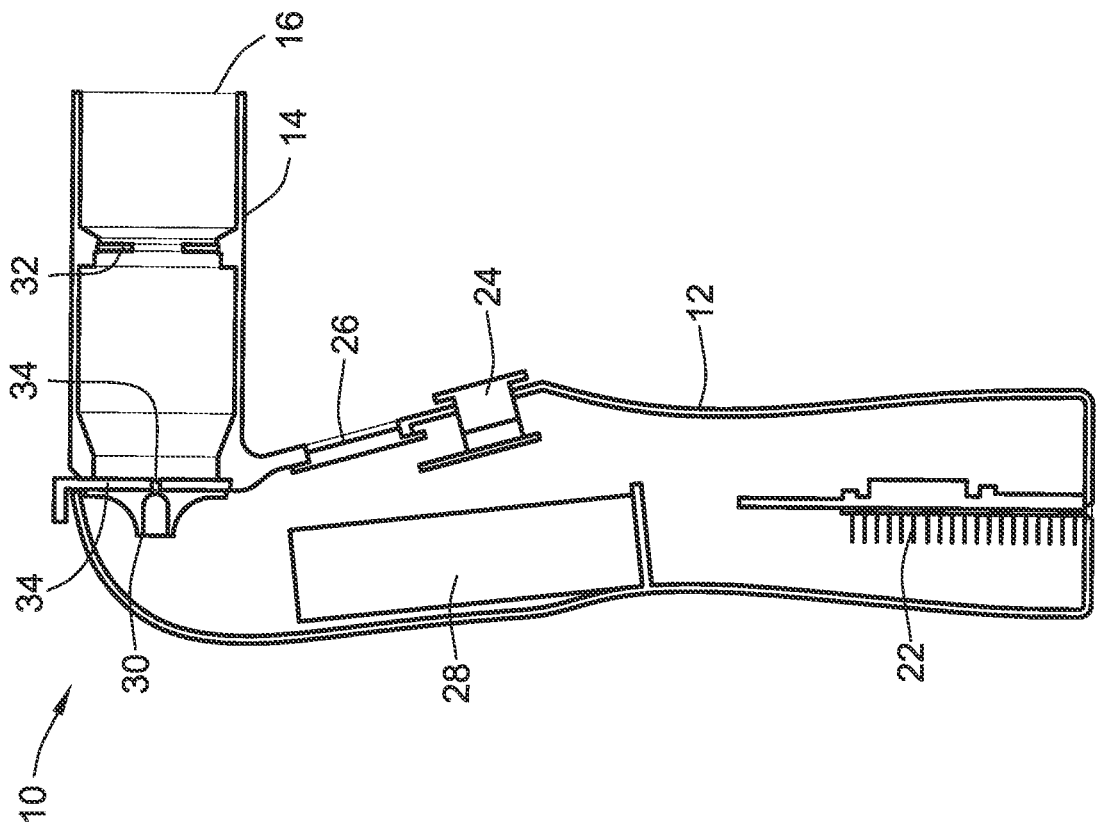
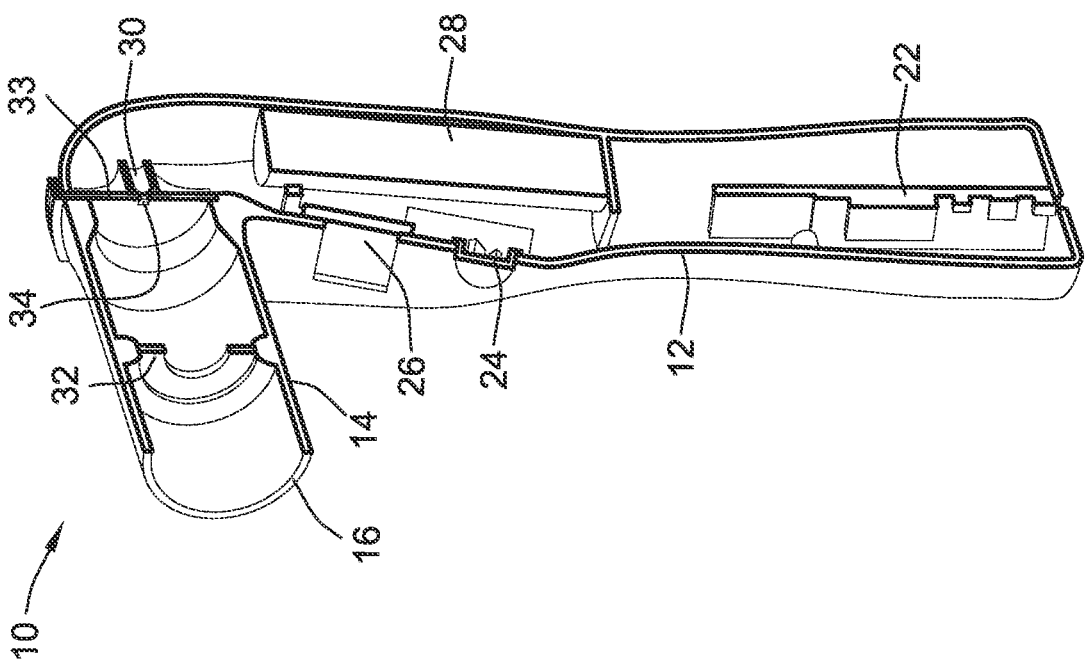

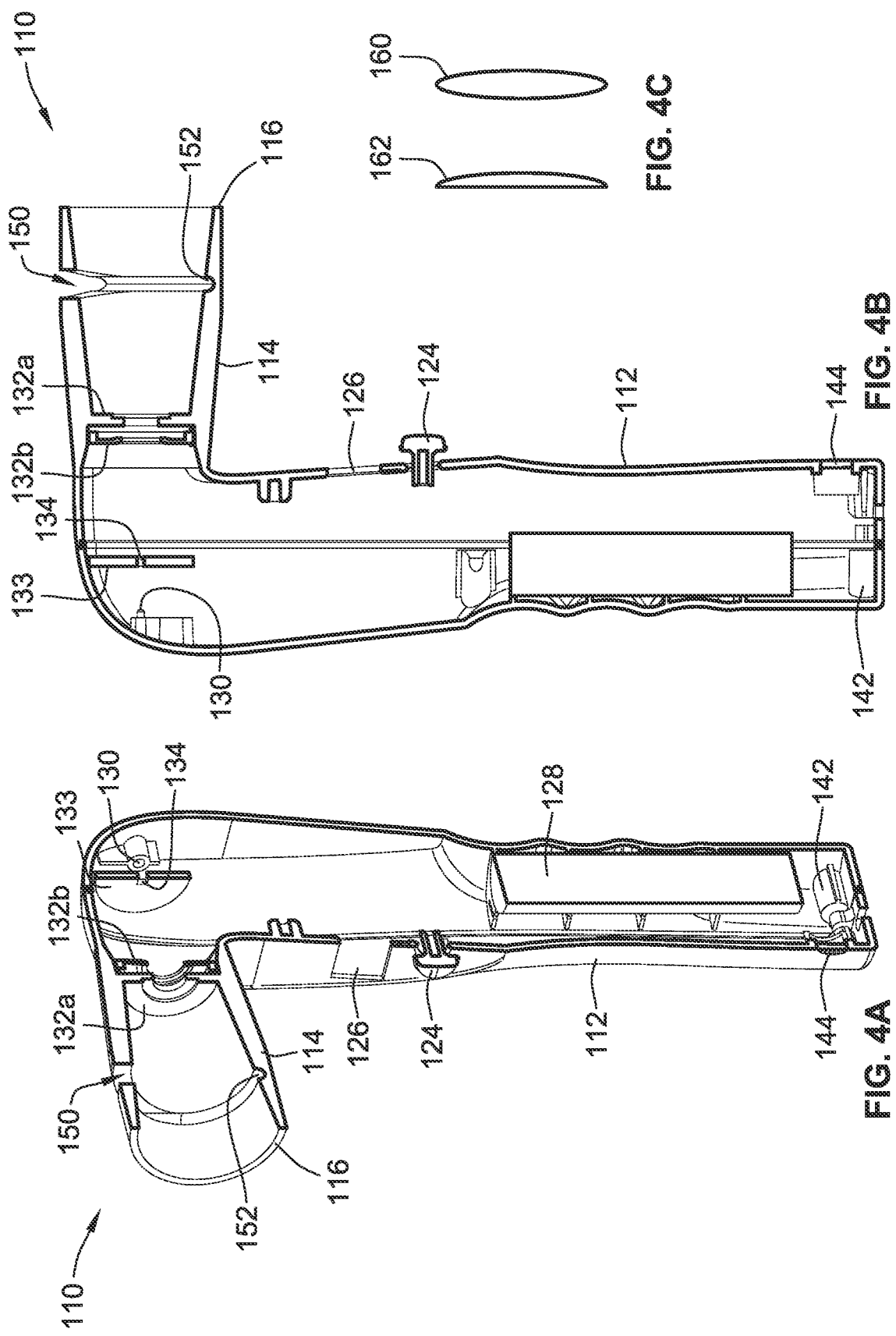

HANDHELD DEVICE FOR MEASURING MACULAR PIGMENT

RELATED APPLICATIONS

This application claims priority under 35 U.S.C. § 119 to U.S. Provisional Application No. 62/705,262, entitled "Handheld Device For Measuring Macular Pigment," and filed on Jun. 18, 2020. The contents of that application are hereby incorporated by reference in their entirety.

FIELD OF INVENTION

The present invention relates to a handheld device that measures characteristics of the patient's eye, such as macular pigment, with a high degree of accuracy.

BACKGROUND OF THE INVENTION

The retina is the layer of nerve cells at the back of the eye, which convert light into nerve signals that are sent to the brain. In humans, and in other primates, the retina has a small yellowish area in the center of the field of vision. That yellowish area is called the "macula." It provides fine-resolution vision in the center of the visual field and is essential to good vision. People who suffer from macular degeneration often lose the ability to read, recognize faces, drive, or walk safely on unfamiliar routes.

"Retinal degeneration" is a descriptive term, which refers to an entire class of eye diseases and disorders. It includes any progressive disorder or disease that causes the macula to gradually degenerate, to a point that substantially impairs or damages eyesight and vision. Several major categories of retinal degeneration are known. These include: (i) age-related macular degeneration, which gradually appears among some people over the age of about 65; (ii) diabetic retinopathy, in which problems with sugar and energy metabolism damage the entire retina, including the macula; (iii) eye diseases that affect the macula due to gene and/or enzyme defects, such as Stargardt's disease, Best's disease, Batten's disease, Sjogren-Larsson syndrome, and various other eye disorders that lead to gradual degeneration of the macula (and possibly other parts of the retina) over a span of time. This is not an exclusive list, and other subclasses and categories also are known. For example, age-related macular degeneration is subdivided into wet and dry forms, depending on whether abnormal and disruptive blood vessel growth is occurring in the structural layers behind the retina.

Awareness has grown of the roles that macular pigment plays in the health and longevity of the macula. Therefore, the two carotenoid pigments that create and provide the macular pigment are discussed below. The macula has a yellowish color because it contains unusually high concentrations of two specific pigments, called zeaxanthin and lutein. Both are carotenoids, similar to beta-carotene but with hydroxy groups coupled to their end rings (the presence of one or more oxygen atoms causes a carotenoid to be categorized as a "xanthophyll", so zeaxanthin and lutein are sometimes referred to as xanthophylls). Both of those two carotenoids are known to be protective and beneficial, in human retinas, by mechanisms that include: (1) absorption of destructive ultraviolet and blue light; and (2) quenching of destructive radicals.

Despite the rarity of zeaxanthin in food sources (zeaxanthin content in typical diets is believed to be less than about 1% of the lutein supply), zeaxanthin concentrations in human blood average about 20% of lutein levels. This suggests the human body does something that indicates a selective preference for zeaxanthin, over lutein. Further, zeaxanthin is even more concentrated in the important center of a healthy human macula that provides fine-resolution vision in humans. There, zeaxanthin is present at levels that average more than twice the concentrations of lutein. By contrast, lutein is present in higher levels around the less-important periphery of the macula. The patterns of deposition suggest that the macula prefers zeaxanthin, and uses lutein when it cannot get enough zeaxanthin.

The present invention provides a handheld device for measuring macular pigment that is light and portable and is easy to operate by the user.

SUMMARY OF THE INVENTION

In one embodiment, an instrument for determining macular pigment of a macula of a human eye includes a housing and a viewing tube. The housing includes a lower hand-held portion with a user-input button and a display for displaying an MPOD score for the user. The lower hand-held portion further includes a battery and electronics for operating the instrument. The viewing tube is coupled to the hand-held portion and terminates in an eye cup. The viewing tube is transverse to the lower hand-held portion and includes a light source for transmitting light in a direction toward the macula. The light source provides two colored lights alternating at an initial frequency that is not perceptible by the user, and the frequency decreases from the initial frequency until the user activates the user-input button in response to a frequency at which the user perceives a flicker of the two colored lights. The perceived frequency is used for determining the MPOD score for the user.

According to one aspect of the invention, a handheld instrument determines the macular pigment in the macula of a human eye. The instrument includes a housing including a lower hand-held portion and a viewing tube. The viewing tube is coupled to the hand-held portion and terminates in an eye cup. The viewing tube is transverse to the lower hand-held portion and transmits light from a light source in a direction toward the macula. In some embodiments, the viewing tube lacks any lenses between the light source and the eye cup. The instrument provides an MPOD (macular pigment optical density) score for the user that correlates to the amount of macular pigment. The MPOD score corresponds to the density of the macular pigment in the retina.

According to another aspect of the invention, an instrument determines the macular pigment of a macula of a human eye. The instrument includes a housing with a lower hand-held portion having a user-input button and a display for displaying an MPOD score for the user. The instrument further includes a viewing tube coupled to the hand-held portion. The viewing tube terminates in an eye cup. The viewing tube is transverse to the lower hand-held portion and transmits light from a light source in a direction toward the macula. The light source is an LED and provides two colored lights alternating at an initial frequency that is not perceptible by the user. The frequency decreases from the initial frequency until the user activates the user-input button in response to a frequency at which the user perceives a flicker of the two colored lights. The frequency at the perceived flicker relates to the MPOD score of the user. The MPOD score correlates to the amount of macular pigment.

In another embodiment, an instrument for determining macular pigment of a macula of a human eye comprises a housing a viewing tube. The housing includes a lower hand-held portion. The lower hand-held portion has a user-input button and a display for displaying an MPOD score for the user. The viewing tube is coupled to the hand-held portion and terminates in an eye cup. The viewing tube is transverse to the lower hand-held portion and has a diameter between about 20 to 35 mm. The viewing tube transmits light from a light source in a direction toward the macula. The light source is an LED and provides two colored lights alternating at an initial frequency that is not perceptible by the user. The frequency decreases from the initial frequency until the user activates the user-input button in response to a frequency at which the user perceives a flicker of the two colored lights. The frequency at the perceived flicker is related to the MPOD score of the user. The device may be used with a plurality of lenses, each of which can be fitted into the viewing tube. The lens may be selected based on the state of the user's eyesight.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 1A is an isometric view of the internal components of the handheld device for measuring macular pigment.

FIG. 1B is a side view of the internal components of the handheld device for measuring macular pigment.

FIG. 4A is an isometric view of the internal components of an alternative handheld device for measuring macular pigment.

FIG. 4B is a side view of the internal components of the alternative handheld device of FIG. 4A.

FIG. 4C is a side view of a pair of possible lends to be used with the handheld device of FIGS. 4A and 4B.

Figure 2:
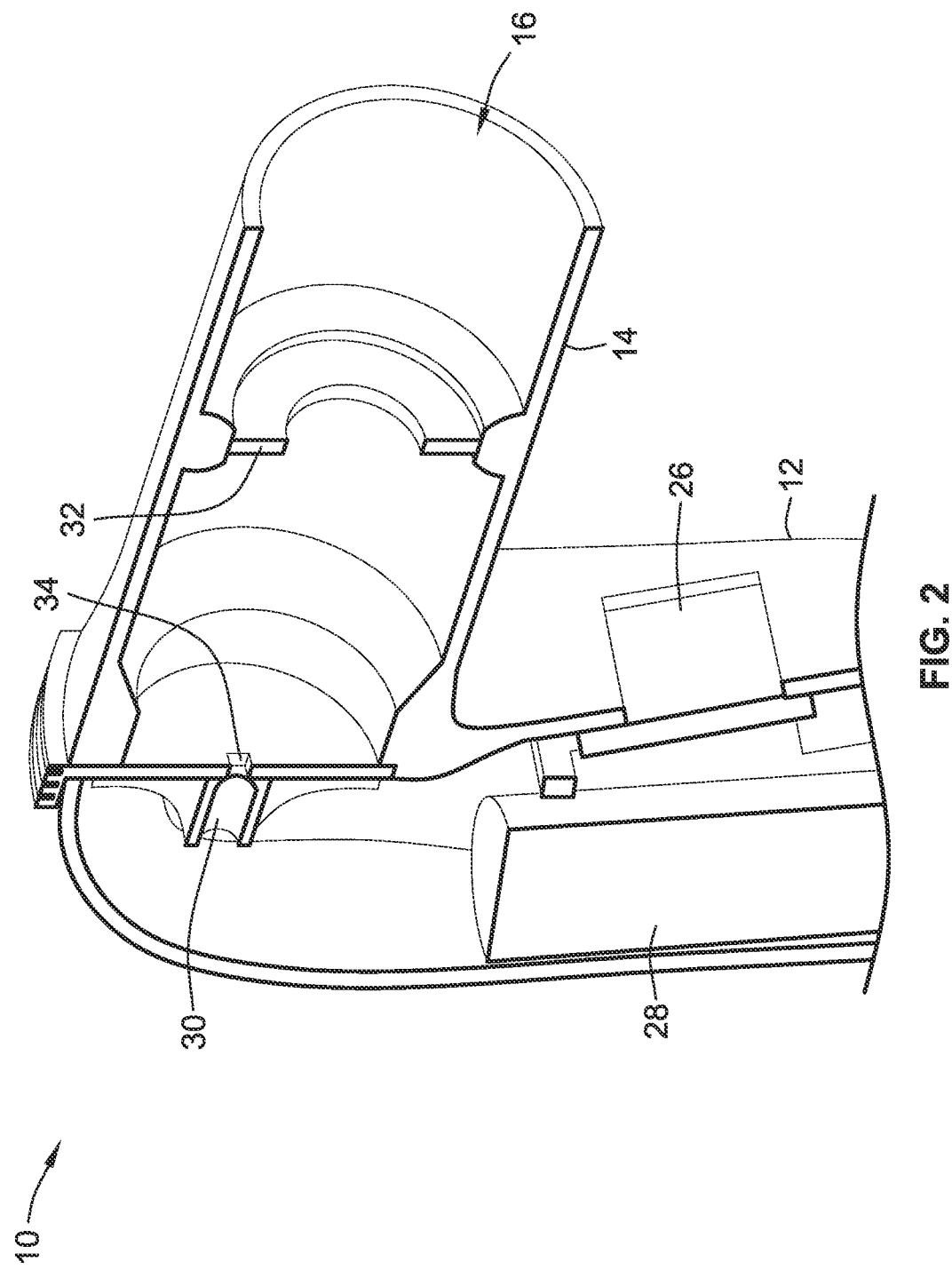
FIG. 2 is an expanded view of the viewing tube barrel of the handheld device of FIGS. 1A and 1B.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The drawings will herein be described in detail with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

FIGS. 1A and 1B illustrate a handheld device 10 for measuring the macular pigment optical density (MPOD) of a user's macular. The device 10 includes a handle 12 that is ergonomically shaped to be received by the user's hand and a viewing tube 14 with a user input region having an eye cup 16 into which the user looks during operation. The axis of the viewing tube 14, which includes the primary optical components of the device 10, is generally perpendicular to the axis of the handle 12.

The handle 12 of the handheld device 10 serves as a housing for the microcontroller 22 that is used for operating the various components and controlling multiple operations simultaneously. The microcontroller 22 preferably has Wi-Fi functionality, Bluetooth functionality, and low-power capabilities. The microcontroller 22 is mounted on a printed circuit board with other components to perform the operations of the handheld device 10. In one preferred embodiment, the microcontroller 22 is a ESP32 chip (manufactured by Espressif).

The handle 12 also includes a button 24 that can be actuated by the user during operation. The button 24 is coupled to the microcontroller 22 and is ergonomically located at a side of the handle 12 to allow the user to easily actuate the button with his or her finger while holding the handle 12. A display 26, which may be an OLED display, is positioned on the handle 12 and is also coupled to the microcontroller 22, allows for the display of various pieces of information to the user regarding the operation of the handheld device 10. The handle 12 incudes the battery 28 needed for operating the entire device 10. For charging the battery 28, the handheld device 10 can be coupled to a separate base docking station or attached to a wire charger. In one embodiment, the battery 28 is preferably a 2200 mAh battery with a voltage regulator that is included in the circuit to boost the battery from 3.3 Volt to 5 Volt. The battery 28 can power MPOD device 10 for a period of several days on a single charge.

FIG. 2 illustrates the viewing tube 14 in more detail. Within the viewing tube 14 of the handheld device 10, there are two different sized apertures—a light ring 32 and an aperture 34 in a blocking wall 33—to help the user focus on a light source 30 situated at the rear of the viewing tube 14. The light source 30 is mounted co-linearly along the center axis of the viewing tube 14 to provide a fixation target for the user. The light ring 32 provides a light-colored (preferably white) background with an inner circular opening through which the user visualizes the light source 30, thereby providing proper contrast to the light source 30.

The light source 30 is preferably a red-green-blue (RGB) LED situated at the rear of the viewing tube 14. The light ring 32 is used to help illuminate the aperture 34 in the blocking wall 33 giving a white wall with the blue/green light source 30 in the center. The front wall of the aperture 34 is preferably a white color. The backside of the light ring 32 facing the light source 30 is also preferably a white wall. The front side of the light ring 32, which faces the user, is preferably a dark color. The light source 30 transmits the input light through the aperture 34, which is adjacent thereto, and through the light ring 32 where it enters the user's eye via the eye cup 16. The operation of the device 10 with the blue and green lights is discussed further below. The red light can be used to alert the user that the test is completed.

The overall inner diameter of the viewing tube 14 is in the range from about 20 to 35 mm, and is preferably about 28 mm in diameter. The LED light source 30 transmits light at an angle of about 1 degree. The aperture 34 preferably has a diameter of about 1.5 mm, while the opening in the light ring 32 has a diameter of about 10 mm. The spacing between the light source 30 and the aperture 34 is about 2 mm. The spacing between the light ring 32 and the blocking wall 33 defining the aperture 34 is typically from about 10 mm to about 50 mm. In one embodiment, the spacing between the light ring 32 and the blocking wall 33 defining the aperture 34 is about 25 mm. The spacing between the light ring 32 and the eye cup 16 is in the range of about 20 mm to 60 mm, which is determined by whether a magnification lens is used and, if so, the power of the magnification. In one embodiment, the ratio of the diameter of the opening in the light ring 32 to the distance between the light ring 32 and the eye cup 16 is about 1:2. Consequently, the user's eye is at a known distance from the LED light source 30 and the background adjacent to the light transmitted from the light source 30 within the user's vision is known.

In one embodiment, the device 10 provides a benefit over known devices because there are no lenses in the optical path between the light source 30 and the user's eye. Rather, the user only visualizes the light source through the openings in the light ring 32 and the aperture 34. The end of the viewing tube 14 may have a piece of glass or plastic so as to seal the inner region of the viewing tube 14 adjacent to the eye cup 16.

Alternatively, the viewing tube 14 may include a lens as the sealing component near the eye cup 16. The lens may assist the user in viewing the light from the light source 30. As discussed in more below with respect to FIG. 4C, the lens may be, for example, between 10-15 diopters. On other embodiments, the lens is from about 5-10 diopters. In a further embodiment, the device 10 may include a kit of barrel extenders that extend the length of the viewing tube 14, with each barrel extender provider a different lens to assist the users with specific lens needs in viewing the light from the light source 30. For example, the lens available in the kit of barrel extenders may be 1 diopter, 3 diopters, and 5 diopters, and each barrel extender may be of a certain length. Each barrel extender may be fastened to the viewing tube 14 via clips or threads.

The handheld device 10 can help track the progression of macular degeneration via MPOD scores. This device 10 is designed to be portable, easy to use, and provide accurate diagnostics. When the device 10 is operated, the display 26 mounted on the handle 12 of the device 10 provides information (alpha-numeric data and graphics) to instruct the user on how to begin the MPOD test and informs the user which eye will be tested. The display 26 instructs the user to place his or her eye onto the eye cup 16 and the testing begins. The display 26 is preferably an OLED display device.

At the start of the test, the LED light source 30 alternates between green and blue light beginning at a frequency of about 60 Hz, which is imperceptible to the user. In other words, the user perceives a constant (non-flickering) blueish-green light. The frequency of the LED light source 30 then decreases until the user can see a flickering effect caused by the alternating colors of green and blue. The user input plus a defined offset (e.g., about 6 Hz) is saved as the new initial frequency for the starting point for the main testing procedure for the user. The defined offset ensures the test starts above the user's perception of flickering, while not wasting testing time as the frequency decreases from a much high frequency. This first step serves to save time in the test procedure. The main test then proceeds and records the user's starting point for the main testing procedure.

For the subsequent tests, the device 10 now changes the decibel ratio between the blue and green LED intensities by 0.2 decibels. The blue light may be decreased while the green light is increased to keep the overall intensity about the same. Using the initial frequency as the new starting frequency, the device 10 begins to reduce by 3-6 Hz per second. When the user sees an observable flicker, he or she presses on the button 24 located on the side of the handle 12 of the device 10, which indicates to the device 10 that the user has perceived the flicker. Again, the starting frequency is changed based on the user's previous input. The device 10 changes the decibel ratio and begins the test again until a local minimum is discovered in their curve of dB ratio versus frequency graph.

Figure 3:
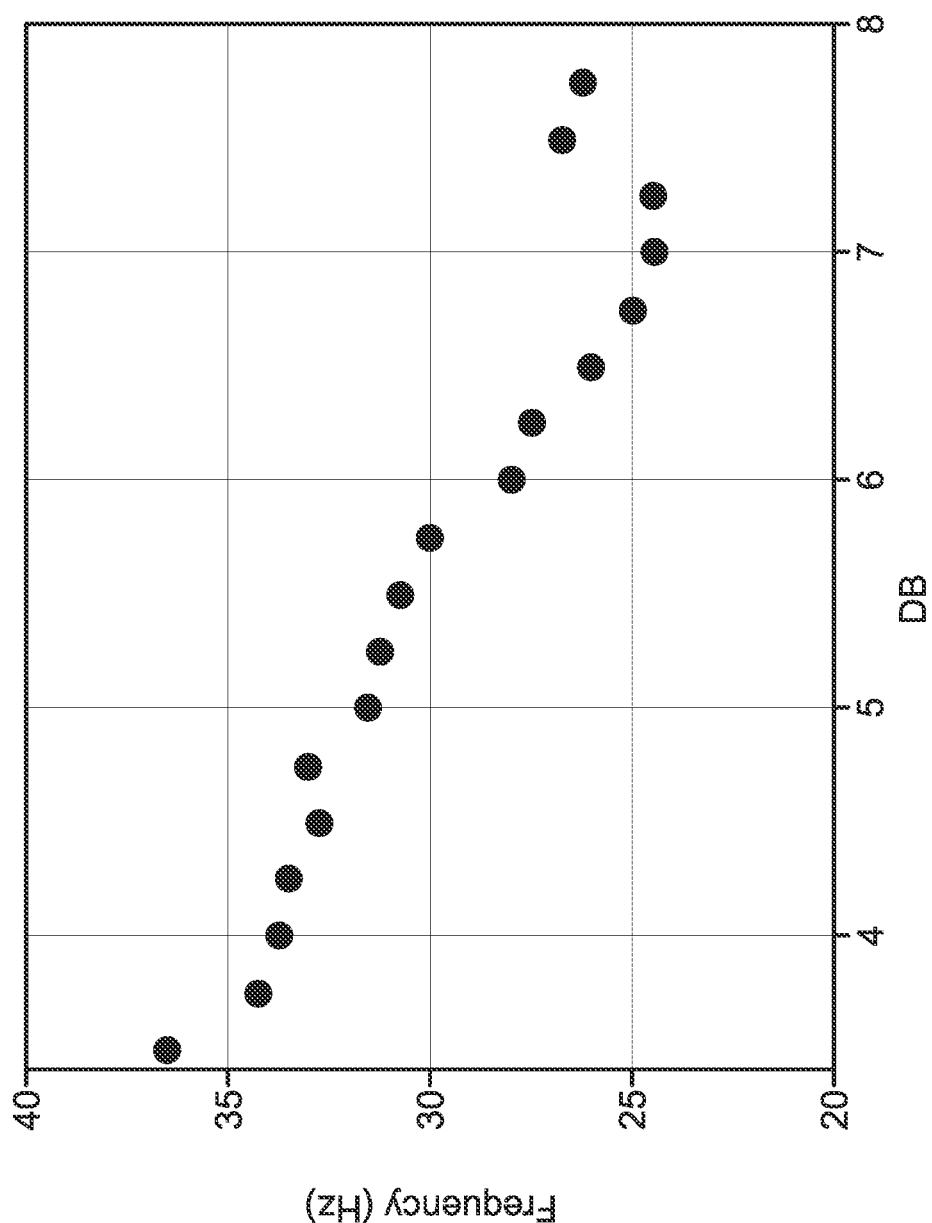
FIG. 3 is an exemplary MPOD graph for a user.

At this point, the test is completed and the MPOD score is calculated and displayed on the OLED display 26. A user's MPOD score is based on how their eye reacts to the flickering that is perceived. A healthy eye will have a minimum frequency value at much higher decibels, as seen as farther right on FIG. 3. In FIG. 3, the minimum value of about 24 Hz is at about 7 decibels. A healthier eye will respond faster to the flicker. These two inputs are used to determine the overall health of a patient's macula. The user is then instructed by the display 26 to use the device 10 on the user's other eye or it will automatically go to sleep due to inactivity.

The user's MPOD score can be stored locally on memory within the device 10. By use of the Wi-Fi and/or Bluetooth communications capability of the microcontroller 22, the MPOD measurements from the device 10 can be transferred to the user's personal mobile phone or device, local storage (e.g., a computer), or cloud storage associated with the user and/or facility that owns the device 10. Preferably, the device 10 can stream the MPOD scores to the cloud for immediate review by a doctor.

Preferably, the device 10 that adapts in real time to the speed of the user's input. If the user is not able to perceive the flicker at high frequencies the device 10 will automatically start each test at lower frequencies to save time during the overall test, as noted above.

The alternating blue-green flicker (other colors of flicker can be used as well) is selected such that there is no temporal overlap between the different colored lights. Alternatively, there can be some overlap between the blue light and green light during the flicker, which can provide the benefit of a more consistent luminosity. This also provides a benefit with a smooth transition during ramp up and ramp down of the LEDs.

The device 10 may also include an age-correction function into this device. As a user ages, their MPOD score will predictably shift down the graph of FIG. 3. Therefore, two individuals with the same MPOD score can have completely different diagnoses. To compensate for the user's age, the device 10 may allow users to input their age.

In another preferred embodiment, the device 10 includes a camera and lens system directly adjacent to the light source 30. The camera provides the ability to take images of the user's retina and macula as the user is engaged in the MPOD test with the device 10. The images can be stored locally and/or transferred from the device 10.

FIGS. 4A and 4B illustrate an alternative MPOD device 110 relative to the MPOD device 10 of FIGS. 1-2. In FIGS. 4A-4B, the reference numerals are listed as 100-series reference numerals that represent structures and features that are similar to the structures and features of the device 10 of FIGS. 1-2 that have two-digit reference numerals. The MPOD device 110 includes a handle 112 and a viewing tube 114. Unlike the device 10 of FIGS. 1-2, the viewing tube 114 flares outwardly, preferably at an angle of less than 10 degrees. In one embodiment, the flare angle of the viewing tube 114 is about 3 degrees.

The handle 112 includes a button 124 that can be actuated by the user during operation. The button 124 is coupled to a microcontroller (not shown in FIGS. 4A-4B) and is ergonomically located at a side of the handle 112 to allow the user to easily actuate the button 124 with his or her finger while holding the handle 112. A display 126, which may be an OLED display, is positioned on the handle 112 to permit the communication of various pieces of information to the user regarding the operation of the MPOD device 110. Unlike FIGS. 1-2, the handle 112 incudes a battery 128 at the lowermost portion of the handle 112, which allows the user to hold the device 110 with more stability because the weight of the battery 128 is shifted to a location where the user grips the handle 112. In one embodiment, the battery 128 can power the MPOD device 110 for a period of several days on a single charge.

In the MPOD device 110, the LED light source 130 in the viewing tube 114 is shifted further away from the eyecup 116. To help the user focus on a light source 130 situated at the rear of the viewing tube 114, there are a pair of light rings 132a and 132b to provide a light-colored background with inner circular openings through which the user visualizes the light source 130, thereby providing proper contrast to the light source 130. The front side of the light ring 132a, which faces the user, is preferably a dark color. A blocking wall 133 with an aperture 134 is located directly in front of the light source 130 in the center of the viewing tube 114. The light source 130 transmits the input light through the aperture 134, which is adjacent thereto, and through the light rings 132a and 132b where it enters the user's eye via the eye cup 116. The operation of the device 110 is preferably with the blue and green lights, as discussed above.

The MPOD device 110 also provides the user with the option for tactile feedback or audio feedback. At the lower portion of the handle 112, a motor 142 creates a vibratory feedback to let the user know that the specific test or test sequence is about to start or is finished. The vibratory feedback from the motor 142 may also be used to inform the user that the user's input via the button 124 has been received. Alternatively, or in addition to the motor 142, the MPOD device 110 may include a speaker 144 to provide audio outputs to the user. The speaker 144 can be used to provide instructions to the user on the operation of the overall (e.g., a tutorial on how the MPOD device 110 operates) or on particular actions needed by the user (e.g., instructing the user to actuate the button 124 when the flicker becomes visible). The speaker 144 can also inform the user if he or she is using the device 110 correctly, or if there is too much shaking or movement of the device 110 (e.g., by use of an internal accelerometer) during operation. In short, like a lighting sequence (e.g. blinking red light) from the LED device 120, the motor 142 and the speaker 144 provide other ways to communicate with the user.

The viewing tube 114 of the MPOD device 110 further includes a slot 150 at a known position along the length of the viewing tube 114. The slot 150 leads into a lower groove 152. The slot 150 and the groove 152 are for receiving a lens, such as the lens 160 of FIG. 4C. In one embodiment, the lens 160 is fitted within the slot 150 with its lower end resting in the lower groove 152 of the viewing tube 114. The lens 160 is permanently positioned fixed within the viewing tube 114. Alternatively, a kit of available lenses 160 and 162 is used with the device 110 and a lens is selected from the kit that works best for the user. The lenses 160, 162 may be, for example, between 10-15 diopters. In other embodiments, the lens 160, 162 are between 5-10 diopters. In a further embodiment, the standard lens 160 used with the device 110 is about 13 diopters, and other lenses 162 in the kit provide values of 12 diopters, 12.5 diopters, 13.5 diopters, and 14 diopters. The clinician can select from these other lenses to best work with the user.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. An instrument for determining macular pigment of a macula of an eye of a user, comprising:
    a housing including a lower hand-held portion with a user-input button configured for actuation by the user and a display for displaying an MPOD score for the user, the lower hand-held portion further including a battery and electronics for operating the instrument; and
    a viewing tube coupled to the hand-held portion and terminating in an eye cup configured to be placed over the eye of the user, the viewing tube being transverse to the lower hand-held portion, the viewing tube including a light source for transmitting light and a blocking wall with an aperture adjacent to the light source, the viewing tube further including a light ring with a center opening, the light ring being located between the blocking wall and the eye cup, the light source is located in the viewing tube such that the light is transmitted through the aperture of the blocking wall, through the center opening of the light ring, and toward the eye cup, the light source providing two colored lights alternating at an initial frequency that is not perceptible by the user, the frequency decreasing from the initial frequency until the user activates the user-input button in response to a frequency at which the user perceives a flicker of the two colored lights, the perceived frequency being used to for determining the MPOD score for the user.

2. The instrument of claim 1, wherein the aperture of the blocking wall is about 2 mm away from the light source.

3. The instrument of claim 1, wherein a diameter of the viewing tube is in a range from 20 mm to 35 mm.

4. The instrument of claim 1, further including a tactile-feedback device or an audio-feedback device that is actuated in response to the user activating the user-input button.

5. The instrument of claim 1, wherein the two colored lights are a blue light and a green light, the blue light and the green light are generally in opposite on-off phases with some overlap at a transition between the phases.

6. The instrument of claim 5, wherein the light source is a multi-colored LED.

7. The instrument of claim 1, wherein the viewing tube includes a slot into which a lens can inserted.

8. The instrument of claim 7, wherein the lens is selected for the user from a kit of lenses having diopter values between 10-15.

9. The instrument of claim 1, wherein the viewing tube is generally perpendicular to the lower hand-held portion.

10. The instrument of claim 1, further including a battery located at a lowermost portion of the lower hand-held portion for providing more stability of the instrument when being held by the user.

11. The instrument of claim 1, wherein a front surface of the blocking wall facing the eyecup is lighter colored, and a front surface of the light ring facing the eyecup is darker colored.

12. The instrument of claim 1, wherein a front surface of the blocking wall facing the eyecup is white.

13. The instrument of claim 1, wherein the light ring emits light of a different color than the two colored lights of the light source.

14. The instrument of claim 13, wherein the light ring illuminates the blocking wall.

15. The instrument of claim 14, wherein the light ring emits white light.

16. The instrument of claim 14, wherein a front surface of the light ring facing the eyecup is darker colored.

17. The instrument of claim 1, wherein the light source transmits the light directly towards the aperture in the blocking wall.

18. The instrument of claim 17, wherein the light source is mounted along a center axis of the viewing tube.

19. The instrument of claim 1, wherein the light source is located at the rear of the viewing tube and spaced away from the blocking wall.

20. The instrument of claim 1, wherein the light source is mounted on the blocking wall.

* * * * *